United States Patent [19] [11] 4,271,836
Bacal et al. [45] Jun. 9, 1981

[54] APPLIANCE FOR CORRECTION OF SPINAL CURVATURES

[75] Inventors: Kazimierz Bacal, Zielona Gora; Lech Wierusz, Swiebodzin, both of Poland

[73] Assignee: Wyzsza Szkola Inzynierska Im. Jurija Gagarina, Zielona Gora, Poland

[21] Appl. No.: 37,123

[22] Filed: May 8, 1979

Related U.S. Application Data

[63] Continuation of Ser. No. 809,047, Jun. 22, 1977, abandoned.

[30] Foreign Application Priority Data

Jun. 28, 1976 [PL] Poland .................................. 190797

[51] Int. Cl.$^3$ .......................... A61B 17/00; A61F 5/00
[52] U.S. Cl. .................................. 128/303 R; 128/69;
128/92 E; 81/302; 29/268
[58] Field of Search ........................ 128/69, 75, 78, 68,
128/68.1, 92 R, 92 B, 92 E, 92 EA, 83, 303 R,
321, 334 R, 92 D, 84 R; 81/302, 396; 29/256,
268; 254/67; 269/238; 433/83, 89, 90

[56] References Cited

U.S. PATENT DOCUMENTS

| Re. 6,364 | 4/1875 | Armstrong | 269/238 |
| 187,551 | 2/1877 | O'Donnell | 254/67 |
| 1,250,245 | 12/1917 | Tollestrup | 254/67 |
| 1,490,063 | 4/1924 | Tower | 269/238 |
| 1,929,026 | 10/1933 | Marcil | 254/67 |
| 2,002,021 | 5/1935 | Rouse | 128/92 EA |
| 2,895,216 | 7/1959 | Hirsch | 29/256 |
| 4,050,464 | 9/1977 | Hall | 128/92 E |

FOREIGN PATENT DOCUMENTS

| 2424458 | 12/1974 | Fed. Rep. of Germany . | |
| 2275679 | 1/1976 | France . | |
| 2289164 | 5/1976 | France . | |
| 2309201 | 11/1976 | France . | |
| 394479 | 7/1965 | Switzerland | 128/92 D |
| 542515 | 1/1977 | U.S.S.R. . | |

OTHER PUBLICATIONS

Zielke K. et al., Special Instruments for Insertion of the Harrington Rod; from Proceedings of 12th Congress of the Internat'l Society of Orthopedic Surgery & Traumatology, 1973.
Harrington, P.; Design & Specifications of Instruments and Terminology; 1968, pp. 1-57.
Harrington, P.; Biomechanics of the Spine, Chandler Memorial lecture; Chicago Orth. Society, 3/10/61.
Diary of 17th Sci. Congress, of Polish Orth. & Traum. Assoc., "Surgical Treatment of Scoliosis by Harring Method," 1970.
Polish Patent Application #P-178,097 2/17/75, Author Unknown.
Zimmer Compression Set., Journal of Bone & Joint Surgery, British vol. 50-B-No. 2; May 1968.

*Primary Examiner*—Robert W. Michell
*Assistant Examiner*—Arthur S. Rose
*Attorney, Agent, or Firm*—Haseltine and Lake

[57] ABSTRACT

This invention relates to an appliance for correction of spinal curvatures, performed in course of treatment by means of surgical struts.

The appliance has a form of a double-arm lever making possible to extend the effective length of the strut placed in the patient's body, whereby one arm of said lever is ended with a holder for clamping the hook of the strut, the other arm being provided with a screw adjusting the spacing of the arms and the displacement of the hook along the strut. This arm is cut longitudinally, one part whereof being provided with a tapped hole wherein said adjusting screw operates, whereas the other part is provided with a port and with a pivot whereon the link mechanism and the pointer of a dynamometer are mounted. The side surface of said arm carries a scale whereover the tip of said pointer travels indicating the value of the force being applied to the operator.

3 Claims, 4 Drawing Figures

APPLIANCE FOR CORRECTION OF SPINAL CURVATURES

This is a continuation of application Ser. No. 809,047 filed June 22, 1977, now abandoned.

This invention relates to an appliance for additional correction of spinal curvatures, being carried out in course of treatment by use of surgical struts.

There is known a method of correction of spinal curvatures consisting in releasing the ill vertebrae by means of a surgical strut placed in the patient's body. Said strut has preferably the form of a rod the ends whereof are placed in the holes of hooks fitted between the according patient's vertebrae. In order to secure a suitable effective length of the strut one of its ends is provided with several conical steps appropriated for fitting the upper hook, or, according to the Polish patent application No. 966 95, with grooves perpendicular to the rod axis, designed for inserting therein a ring fixing the position of the hook and securing it against any displacement.

The investigations carried out recently by the surgeons proved that after a suitable period of therapy it follows a loosening of vertebrae, making possible to perform an additional correction of the distorted spine, by extending the effective length of the strut. Said extension may be achieved by a displacement of the hook caught at a suitable place of the spine, after previous surgical uncovering of a small operation area.

The aim of the invention is to make possible to perform said additional correction, and the object of the invention is the design of a simple appliance admitting to displace the hook on the strut with simultaneous determination of the force developed by the resistance of the spine to be straightened.

This object has been achieved by designing an appliance in a form of a lever provided with a holder for displacing a hook in a strut.

The appliance has two arms pivotally connected with each other by means of a articulated joint so that when sections of the arms, which are situated at one side of the joint, approach each other, then the sections of the arms, which are situated in the same plane at the opposite side of the joint move away from each other.

One of the sections of the first arm has a jaw at its end and is also provided with a second jaw connected thereto, so that the jaws together form a holder for a hook and co-operate with each other in a plane perpendicular to the plane of the displacement of the arms of the appliance. The distance between jaws is set by an adjusting screw. Each of the jaws is provided with a pin from the side of the other jaw. The pins of both jaws of the holder are placed in holes made in the lateral surface of the hook placed on the strut and protect the jaws against slipping off the hook. The section of the second arm, situated at the same side of the articulated joint connecting the arms, is provided with a recess in which the end of the strut placed in the patient's body is located.

The second section of the second arm is cut longitudinally and forms two parts. One of the parts is provided with an untapped port, the other one is provided with a threaded hole. An adjusting screw is placed in both holes which set the spacing of the arms. On the untapped part, a known dynamometer is fixed to the pin, which shows the resisting force of the spine being straightened.

The holder mounted on the first arm consists of two jaws connected with an articulated joint, the one whereof constitutes the end of the arm, the other one being provided with the adjusting screw. Screwing said screw in causes clamping of said jaws on the hook of the strut.

In order to secure the hook against slipping from the jaws each thereof is provided with entering into the holes of the hook.

The appliance according to the invention is simple in design and independent in use. Its application admits to achieve an additional correction of the spinal curvature through extending the effective length of the strut placed in the patient's body, and enables an additional relieving of the ill vertebrae. The measurement of the resistance force of the spine makes possible to increase gradually, uniformly, in strictly controlled way, and thus safely, the dilatation.

The invention will be now explained more particularly by means of an exemplary embodiment, with reference to the accompanying drawing, wherein.

Figure 1:
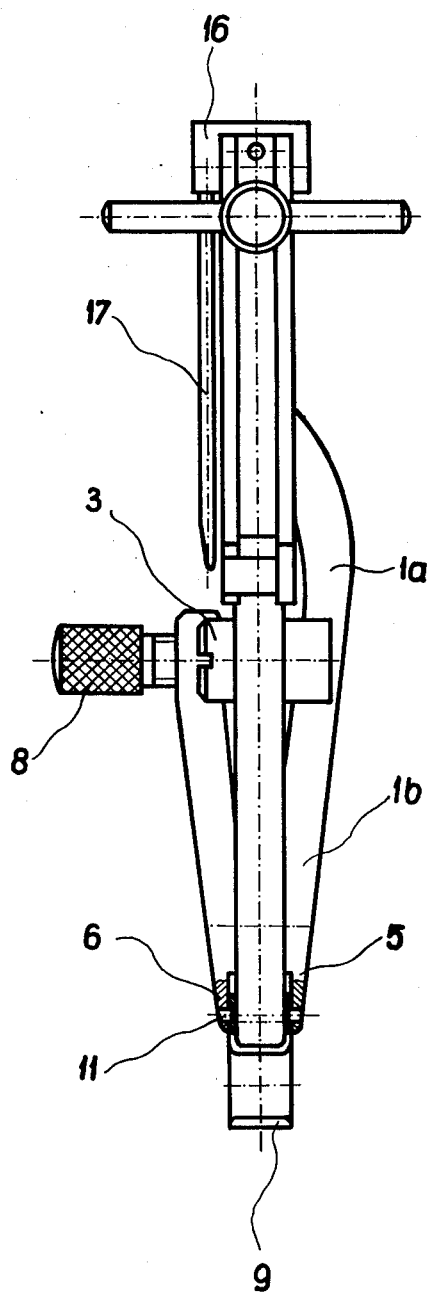
FIG. 1 is the front view of the appliance according to the invention.
Figure 2:
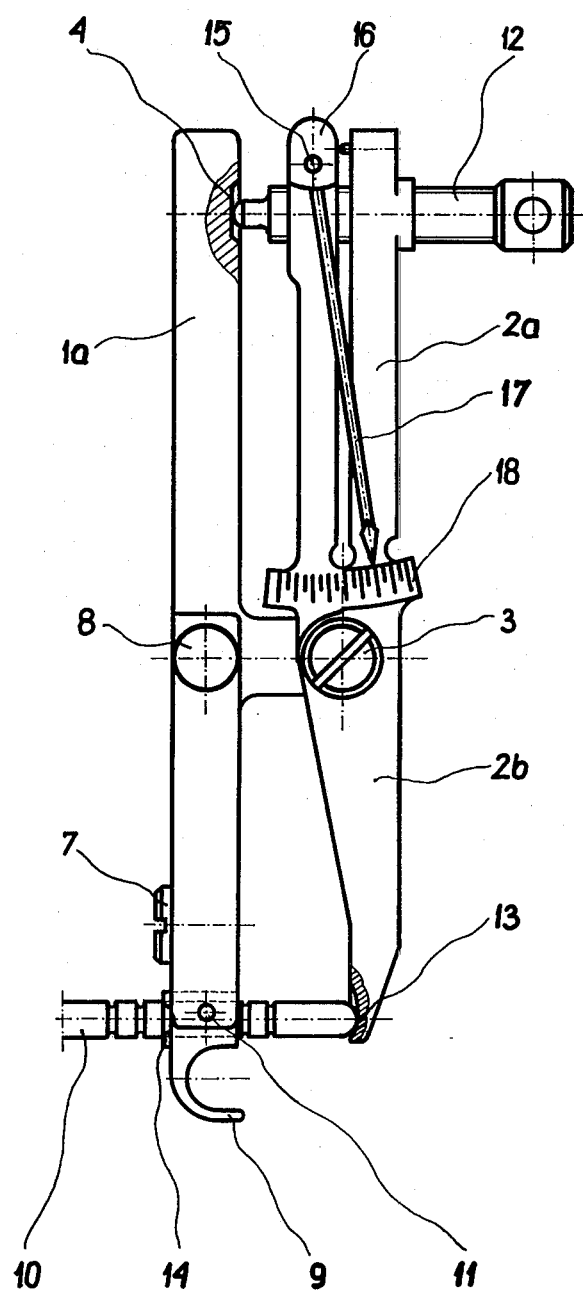
FIG. 2 is the side view of said appliance.
Figure 3:
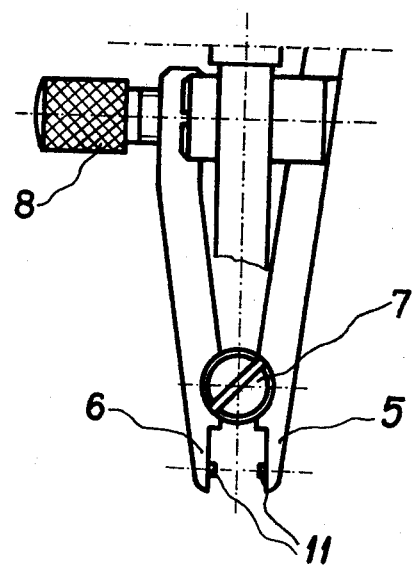
FIG. 3 shows the section 1b of the arm, forming a holder of a hook.
Figure 4:
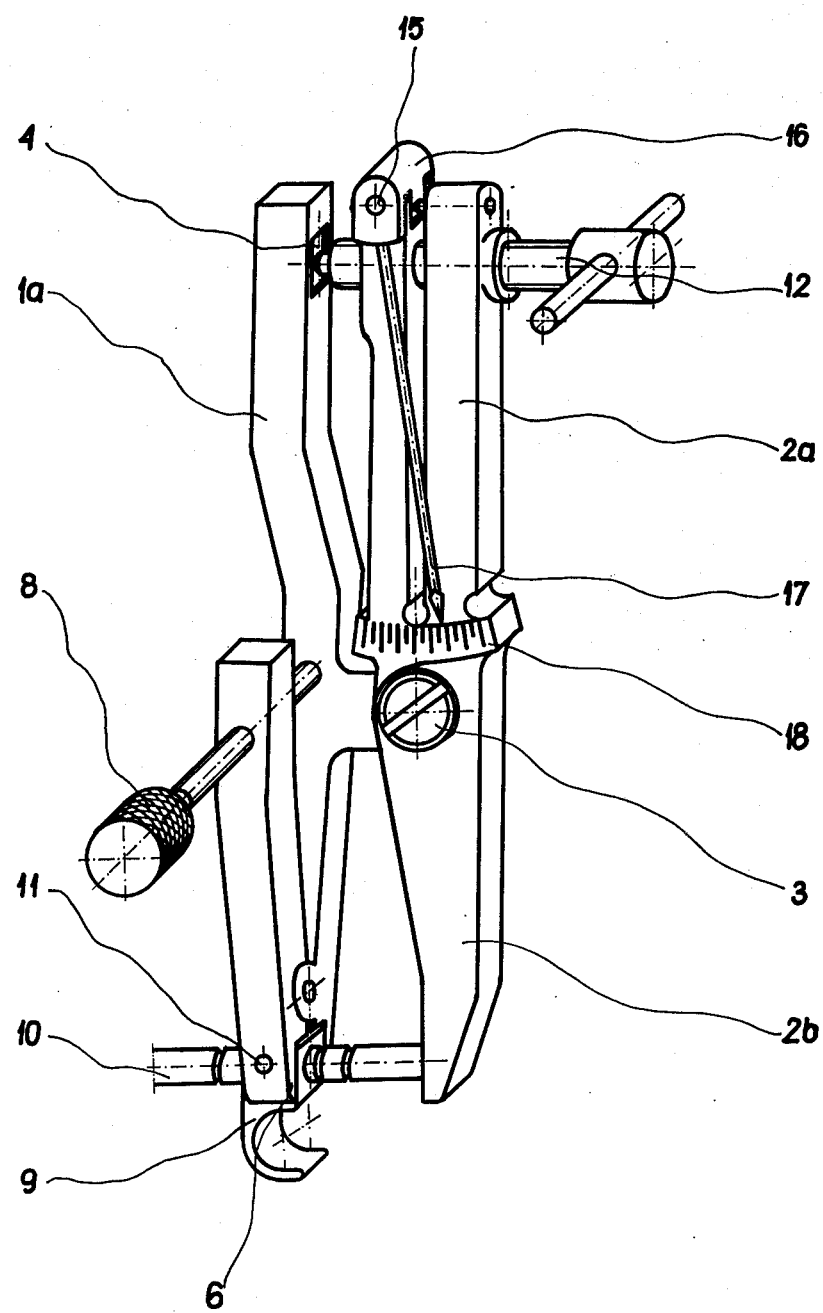
FIG. 4 illustrates the appliance in isometric projection.

The appliance is designed in form of a lever having especially shaped arms fitted over the articulated joint 3, dividing these arms into sections 1a, 1b, and 2a, 2b.

The section 1a of the arm is at its ends provided on its inner side with a recess 4, the section 1b has a termination constituting the jaw 5 of the holder. The jaw 6 forming the other member of the holder is mounted to the section of arm 1b by means of the articulated joint 7, and it is provided with a tapped hole wherein the screw 8 is arranged aimed at clamping the jaws 5 and 6 on the hook 9 of the strut 10 placed in the patient's body. The jaws 5 and 6 are on their inner side provided with pins 11 securing the hook 9 against slipping out of the holder.

The section of arm 2a is longitudinally cut into two parts, whereby one of its parts is provided with a tapped hole wherein the screw 12 operates, adjusting the spacing of the arms of the appliance, the other part having a port with a diameter larger than that of the screw 12 passing therethrough. The section of the arm 26 is from its inner side provided with a recess 13 wherein the end of the strut abuts in course of performing of an additional dilatation. After displacing the hook 9 along the strut 10 its position gets secured by means of the ring 14. The part of the section of the arm 2a, having the port, is provided with a pivot 15, whereon the link mechanism 16 and the pointer 17 of the dynamometer is mounted. The tip of the pointer 17 travels over the scale 18 applied on the side surface of the section of the arm 2a and calibrated accordingly to the value of the resistance force of the spine to be straightened.

What is claimed is:

1. An improved appliance for correction of spinal curvatures in the course of placing a surgical strut in a patient's body comprising, a first elongated arm having a first end portion and a second end portion, said second end portion of said first arm comprising means for releasably securing said first arm to a vertebral bone hook, a second elongated arm having a first end portion and a second end portion, said first arm being pivotally connected to said second arm at a point on said first arm intermediate said first and second end portions of said first arm to a point on said second arm intermediate said first and second end portions of said second arm, said pivotal connection being such that when said arms are pivoted with respect to one another, the movement of both of said arms is parallel to a single plane, said pivotal connection further being such that when said first portions of said first and and second arms are moved away from one another, said second portions of said first and second arms move towards one another, said second end portion of said second arm including a recessed portion adapted to receive the end of a surgical strut and shaped to prevent movement of the strut through, along the length of and to the sides of the second arm, said recessed portion being positioned such that it faces and is aligned with said securing means of said second end portion of said first arm, and screw adjustment means provided on said first end portion of said second arm, cooperating with said first end portion of said first arm for urging said first end portions apart from one another.

2. An appliance as claimed in claim 1, wherein: each of said end portions is provided from the side of the other with a pin, and both end portions together with a screw form a holder for clamping a hook of a surgical strut to be placed into the patient's body.

3. An appliance as claimed in claim 1, wherein: said first end portion of said second arm is cut longitudinally and one of its parts is provided with an untapped port and the other part is provided with a tapped hole, and in both of said holes there is provided an adjusting screw, whereas said second end portion of said second arm is provided with a recess.

* * * * *